United States Patent [19]

Bank et al.

[11] Patent Number: 4,924,022
[45] Date of Patent: May 8, 1990

[54] METHOD FOR PREPARATION OF ORGANOALKOXYSILANES

[75] Inventors: Howard M. Bank, Saginaw County, Mich.; Robert A. Petrisko, Maricopa County, Ariz.

[73] Assignee: Dow Corning Corporation, Midland, Mich.

[21] Appl. No.: 417,128

[22] Filed: Oct. 4, 1989

[51] Int. Cl.$^5$ ................................................ C07F 7/18
[52] U.S. Cl. ................................................ 556/471
[58] Field of Search ........................................ 556/471

[56] References Cited

U.S. PATENT DOCUMENTS

| | | | |
|---|---|---|---|
| 3,448,138 | 6/1969 | De Wit | 556/471 |
| 3,651,117 | 3/1972 | Bennett | 556/471 X |
| 3,792,071 | 2/1974 | Nitzsche et al. | 260/448.8 R |
| 4,039,567 | 8/1977 | Kotzsch et al. | 260/448.8 R |
| 4,228,092 | 10/1980 | Kötzsch et al. | 556/471 X |
| 4,298,753 | 11/1981 | Schinabeck et al. | 556/425 |
| 4,421,926 | 12/1983 | Tolentino | 556/471 |
| 4,471,133 | 9/1984 | Hallgren | 556/471 |
| 4,506,087 | 3/1985 | Fischer et al. | 556/471 |
| 4,642,363 | 2/1987 | Groh et al. | 556/471 |

*Primary Examiner*—Paul F. Shaver
*Attorney, Agent, or Firm*—Robert L. McKellar

[57] ABSTRACT

Disclosed is a one reactor, continuous system for the manufacture of organoalkoxysilanes. The reactor consists of a fractionating means that allows for completion of the reaction and separation of the HCl formed as a by-product. Also disclosed is a means for removing or reducing any residual hydrolyzable chloride or other acids in the organoalkoxysilanes using ion exchange resins.

24 Claims, No Drawings

METHOD FOR PREPARATION OF ORGANOALKOXYSILANES

This invention relates to a continuous process for producing organoalkoxysilanes in which the simultaneous reaction and removal of by products results in the reduction of unwanted side reactions and elimination of gel formation. This invention also relates to a method for reduction of acid in the resulting organoalkoxysilane.

BACKGROUND OF THE INVENTION

Methods for production of organochlorosilanes are well known in the art. One such method used to produce an organochlorosilane is by reacting a chlorosilane of the formula $R_aCl_{(3-a)}SiH$ with unsaturated olefinic material in the presence of a platinum catalyst wherein R is independently selected from the hydrogen atom, an alkyl group containing 1 to 6 carbons, and an aryl group containing 6 to 10 carbons and a has the value of 0 to 2. The organoalkoxysilane is then produced by the alkoxylation (reaction with an alcohol) of the organochlorosilane with hydrochloric acid being produced as a by-product.

The alkoxylation of acrylate functional chlorosilanes, in particular, is difficult due to numerous side reactions that can occur. These side reactions can occur because of the reaction conditions, reaction of the by-products or impurities, or instability of the acrylate group from undergoing polymerization. These side reactions can result in the formation of methyl chloride, methyl methacrylate, other toxic materials, and high molecular weight polymers or gels. Other organochlorosilanes can be difficult to alkoxylate because of reactive or sensitive organofunctional groups that react or decompose in the presence of certain process conditions.

During alkoxylation of organoalkoxysilanes it is essential to remove the HCl by-product to prevent many of the possible side reactions and product contamination. High temperatures, in conjunction with some contaminants, can also be disastrous.

Methods of alkoxylation known in the art include the use of batch and continuous processes. Although batch processing is applicable for making alkoxysilanes, the use of a solvent, higher temperatures, or an acid acceptor may be required to ensure complete separation of the HCl from the product or to minimize the contact time between the HCl and the product. Although these process aides can be applied to continuous processes, operation without them is possible. Because of this it is preferred that the materials be made in a continuous manner.

Methods for alkoxylation of chlorosilanes are well known in the art. However, many of these methods are not applicable to the production of acryloxyorganoalkoxysilanes or organoalkoxysilanes as their operating parameters could result in side reactions, by product formation or gels. For example, Kotzsch et al., U.S. Pat. No. 4,039.567, teaches a continuous method for making alkoxysilanes in which the chlorosilane and alcohol are fed in liquid form and in stoichiometric amounts. This method requires that the reaction mixture be maintained at its boiling point. Because of higher boiling points of most organoalkoxysilanes numerous side reactions would occur if sensitive materials were employed in this method.

Hallgren, U.S. Pat. No. 4,471,133, also teaches a similar method to that of Kotzsch, however, the silane is fed only in the vapor form and alkoxylation of only a limited number of organoalkoxysilanes are taught. Again, the heat required to vaporize the silane could result in side reactions if reactive organochlorosilanes were employed in this method.

Another method for alkoxylation of organochlorosilanes is taught by Nitzsche et al. in U.S. Pat. No. 3,792,071. This method comprises a one column system in which the chlorosilane is fed in the liquid form and any alcohol is fed in a gaseous (vaporized) state. An excess of the alcohol is initially fed to create reflux in the head of the column followed by the feeding of only amounts necessary to achieve a complete reaction. To maintain the reflux the column must be heated or higher temperatures must be obtained in the reboiler.

Several other continuous methods for the production of organoalkoxysilanes are known in the art. One such method uses a two reactor system as described by Schinabeck et al., U.S. Pat. No. 4,298,753. The first reactor, a stirred vessel or tube type, is used to partially react the chlorosilane while the second reactor, a fractional distillation type, is used to complete the reaction. Because the HCl is in contact with the material in the first reactor the probability of side reactions occurring appears to be high although it appears that this is reduced by cooling the first reactor. It is also vague as to how and to what extent the HCl is removed prior to its introduction into the second reactor where higher temperatures are necessitated to complete the reaction.

Fischer et al., U.S. Pat. No. 4,506,087, teaches another two reactor system. In this system, the alcohol is fed into the second reactor and the unreacted amount is condensed and recycled into the first reactor. Again the HCl is not immediately removed from the reaction mixture in the first reactor.

It is an object of this invention to provide a method for producing organoalkoxysilanes by the alkoxylation of organochlorosilanes.

It is further an object of this invention to provide a method for producing organoalkoxysilanes in which the formation of gels and undesirable impurities is minimized through raw materials, process conditions and process equipment.

It is further an object of this invention to provide a continuous method for producing organoalkoxysilanes in which only one reactor is required.

It is further an object of this invention to provide a method for removing or reducing hydrolyzable chloride and other acids in the organoalkoxysilanes.

THE INVENTION

The chemistry of alkoxylation of organochlorosilanes is very complex, being dependent on the purity of the organochlorosilane, the conditions under which the reaction takes place and the ease of removal of the HCl formed in the reaction process. The objects of this invention are achieved by a combination of raw materials, process conditions, and process equipment.

The organochlorosilanes and organoalkoxysilanes of this invention are exemplified by the formula

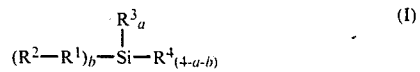

$$(R^2-R^1)_b-\underset{\underset{R^3{}_a}{|}}{Si}-R^4{}_{(4-a-b)} \quad (I)$$

wherein $R^1$ is selected from an saturated or unsaturated alkylene group containing 1 to 10 carbons, an arylene group containing 6 to 10 carbons; any of said groups containing one or more ether oxygen atoms within aliphatic segments thereof; $R^2$ is selected from the hydrogen atom, a halide atom, the nitrogen atom and an alkyl group consisting of 1 to 6 carbons optionally containing one or more of acryloxy, methacryloxy, carboxy, or ester functional groups; $R^3$ is independently selected from the hydrogen atom, an alkyl group containing 1 to 6 carbons and an aryl group containing 6 to 10 carbons; $R^4$ is independently selected from the chlorine atom or the alkoxy group; a has the value of 0 to 3 and b has the value of 0 to 1 such that the sum of a+b does not exceed 3. Completion of reaction is defined as when substantially all $R^4$ present on the molecule are represented by the alkoxy group.

Alcohols useful in this invention are of the general formula $HOR^5$ wherein $R^5$ is selected from a straight or branched chain alkyl group containing 1 to 6 carbons. The alkoxy group is produced when the hydrogen atom is removed from the molecule and is substituted by $-OR^5$. Alcohols useful in this invention should boil at a temperature lower that the organoalkoxysilane formed from them. Alcohols most commonly employed by the method of this invention are methanol and ethanol.

Some side reactions and formation of some by-products can be initially decreased by the use of an organochlorosilane which has been distilled. Distillation of the organochlorosilane is applied to remove impurities that include lower or higher boiling matter, or unreacted raw materials, impurities from the starting materials and residual platinum. Distillation will result in a material essentially free of reactants that could result in or possibly catalyze some of the side reactions. The function of using a distilled material is also to remove higher molecular weight molecules that could precipitate out during the alkoxylation process. The use of distilled organochlorosilanes is preferred, especially when acrylate containing materials are used.

The distillation of the organochlorosilane need not be achieved by complicated or novel methods nor is the separation critical. Distillation can be achieved by such techniques such as thin film evaporation, flash evaporation, batch or continuous distillation and other such methods employed in the art.

The addition of a compound that inhibits polymerization or stabilizes the organofunctional silane may be required during the alkoxylation process especially when acryloxy or methacryloxy (herein referred to only as acryloxy) groups are present. The acryloxy groups may undergo polymerization even at the mildest conditions achieved during the alkoxylation. Examples of inhibitors useful for preventing polymerization of acryloxy functional silanes are diphenylphenylenediamine, phenothiazine, monomethyl ether of hydroquinone or anilinophenol or other phenolic inhibitors. The preferred inhibitor for this invention is phenothiazine. Phenothiazine may already be present in the acryloxyorganochlorosilane (depending on the process used to produce it) or may be added to the acryloxyorganochlorosilane at any point prior to its introduction into the column. Levels of 50 to 2500 parts per million parts organochlorosilane should be added with the preferred level being 100 to 1000 parts per million parts organochlorosilane.

The alkoxylation reaction should be carried out in equipment which can simultaneously provide for the reaction between the organochlorosilane and alcohol and the removal of the hydrochloric acid. One such example, and that which is preferred for this invention, is a column suitable for fractionation. The column should be designed to allow for proper separation of the HCl away from the organoalkoxysilane and to provide enough residence time for the reaction to go to completion. The column should be equipped with a means of providing heat to the material at a sump portion of the column and a means of cooling and more preferably condensing the material at the head of the column. Multiple column systems that simulate a one column system are also useful in this invention.

Means for providing heat can be exemplified by such means as a reboiler. Types of reboilers useful and known in the art are a kettle reboiler, vertical and horizontal thermosiphon reboiler, forced recirculation reboiler, or others. Partial, single and multi-component reboiler systems can be used. The medium for providing the heat in the heat means can be steam, electric or other depending on the temperature desired.

Means for cooling can be exemplified by single or multi-component cooling systems comprising air cooled overhead condensers, horizontal and vertical in-shell condensers, horizontal or vertical in-tube condensers and others. The medium for providing the cooling in the condenser can be air, water, glycol, known refrigerants and others.

The column should be equipped with vapor/liquid contacting devices suitable for the separation and reaction needs and also for preventing the formation and collection of gels. These contacting devise may be further exemplified by trays or packing which are known in the art and are commercially available. The preferred contacting devices of this invention are those relating to trays however packing has been found suitable for this invention. Columns that contain a combination of packing and trays are also suitable. The preferred type of tray for this invention is that of the bubble cap Operation of the column and design of the contacting devices should prevent the allowance of non-wetted surfaces (dry spots) as it is believed that undesired reactions will be enhanced on those surfaces. This can be achieved by maintaining a constant liquid flow throughout the column and ensuring that the column temperatures do not become too hot.

Start-up of the process can be aided by the use of a heel, consisting of the organoalkoxysilane, in the heating means so that the desired operation temperature can be achieved in the heating means at the start of the operation. The use of the organoalkoxysilane is not necessary, however, it is preferred. Other materials which are non-reactive with the organochlorosilane, organoalkoxysilane, methanol or hydrochloric acid can also be used as a heel, in the heat means during the start-up. These materials should boil at a temperature above the desired operating temperature. If a material other than the organoalkoxysilane is used it may desirable to separate that material from the final product through distillation means or by disposing of the product contaminated with the heel material. If the organochlorosilane is used as the heel, material from the sump portion of the column should be recycled with the feed until complete reaction has been achieved. Materials suitable for the heel can be exemplified by the organoalkoxysilane, similar organoalkoxysilanes, the organochlorosilane, similar organochlorosilanes, solvents or any combination thereof.

The method for introducing the feeds into the column has been found to also increase the degree of completion of the reaction. The alcohol can be fed into the column in either a liquid or a vapor phase or a combination of both. The preferred method is to feed the alcohol at levels such that 60 to 100 percent can be vapor and 0 to 40 percent can be liquid. The alcohol in the liquid phase should be fed into the upper portion of the column while the alcohol in the vapor phase should be fed into the lower portion of the column.

It is preferable, but not necessary, to mix the liquid alcohol with the organochlorosilane prior to initiating it into the column or to feed them into the same location. The process for this mixing can be obtained by using the same pipe or mechanical means to feed them into the column or supplying them independently into an agitated vessel. It is preferred that the liquid alcohol and feed be introduced into the column at the head while the alcohol being fed in the vapor form be introduced into the column at a point above the heat source and below the bottom contacting device.

Alcohol should be continuously supplied in excess of the theoretical amount required to complete the reaction. This excess should not exceed 125 percent of the theoretical amount required to obtain a complete reaction. The preferred excess of this invention is from 101 to 115 percent of the theoretical amount. The use of theoretical amounts of alcohol or a slight excess below the desired levels may result in a highly acidic product.

Operating conditions have also been found to enhance the completion of the reaction. The reboiler temperature should be maintained at temperatures above the boiling point of the alcohol and below the boiling point of the organoalkoxysilane when operating at atmospheric pressures. If the column is operated under vacuum or at pressures above that of atmospheric the temperatures should be adjusted accordingly. It is preferred that the temperature of the column be operated at a point below the boiling point of the organoalkoxysilane but at a temperature high enough to allow the reaction to proceed to completion. It is also desired that at least the lower $\frac{1}{3}$ of the column be maintained at a temperature above the boiling point of the alcohol, preferably within approximately 20° C. of the boiling point of the alcohol. The preferred temperature range in the lower $\frac{1}{3}$ of the column when using methanol is 73° C. to 77° C. Temperatures in the remaining upper $\frac{2}{3}$ of the column, particularly in the head of the column, may be well below the boiling point of the alcohol. By maintaining such conditions during operation there should be no reflux of alcohol in the head of the column.

The basic principles of the operation of this invention comprises feeding a liquid organochlorosilane and excess liquid/vapor alcohol into a fractionation means comprised of contacting devises, heat means and cooling means. The operating temperature in the heat means is maintained above the boiling point of the alcohol but below that of the organochlorosilane. The temperature should be such that there is no reflux of alcohol in the head of the column. The organochlorosilane may or may not be distilled prior to its use and it may or may not contain a compound that can inhibit polymerization of the organochlorosilane or organoalkoxysilane.

The organoalkoxysilanes produced by this invention sometimes contain small amounts of residual hydrolyzable chloride or other acids such as methacrylic acid. Although it is believed that these acids are in quantities low enough that the stability of the material is not affected, it may be undesirable for certain applications or for aesthetic reasons to have this acid present. A method to reduce the acid present in the organoalkoxysilane is achieved by contacting the organoalkoxysilane with an ion exchange resin. Ion exchange resins, in particular anionic exchange resins, comprised of tertiary amines and useful in nonaqueous media are preferable for this invention. In particular Amberlyst A-21 produced by the Rohm and Haas Corp., Philadelphia, Pa., and Dowex MWA-1 produced by Dow Chemical Company, Midland, Mich., have been found to be useful.

The organoalkoxysilane may be treated to reduce the acid as it directly comes off of the bottom of the reactor or the organoalkoxysilane may be collected, stored and treated at a later time to reduce any acid. The ion exchange resins useful in this invention are charged into a column or other containing source to produce a bed of appropriate size for the amount of material to be processed. When the ion exchange resin is contained in a base of water, this should be displaced by first flowing methanol through the bed. The methanol is then displaced by a flow of nitrogen until the bed is dry. The removal of all water, methanol, or other hydroxylic materials from the ion exchange resin is important to prevent undesired reactions and/or the formation of gels. Once the ion exchange media has been prepared the organoalkoxysilane is fed so that it contacts the resin bed and flows through the bed at a rate such as to maintain a liquid level in the bed. The bed should be renewed or changed when acid levels of those greater than desired are contained in the material leaving the bed.

The organoalkoxysilanes produced by this invention and treated thereafter to remove acid contamination may be further exemplified by, but not limited to, those which have unsaturated or other highly reactive sites, or are sensitive to decomposition at higher temperatures. These compounds may be further exemplified by vinyltrimethoxysilane, isobutyltrimethoxysilane, chloropropyltrimethoxysilane, chloroisobutylmethyldimethoxysilane, chloropropylmethyldimethoxysilane, hexenylmethyldimethoxysilane, 3-methacryloxypropyltrimethoxysilane, methyl-3-methyl- dimethoxysilyl-2-methylpropionate, cyanoethyltrimethoxysilane, phenyltrimethoxysilane, propyltrimethoxysilane, trifluoropropylmethyldimethoxysilane and others.

So that those skilled in the art can understand and appreciate the invention taught herein the following examples are presented, it being understood that these examples should not be used to limit the scope of this invention over the limitations found in the claims attached hereto.

EXAMPLE 1

Distilled, inhibited 3-methacryloxypropyltrichlorosilane (A) was prepared according to U.S. Pat. No. 4,780,555 and was found to have a GLC purity of 98.52 percent monomer.

The apparatus used was a two sectioned, 29 tray, bubble cap column. The upper section contained 20 bubble Caps spaced at 1 inch intervals while the bottom column contained 9 bubble caps spaced at 1 inch intervals. Seventeen inches above the top bubble cap tray was a volatile condensation unit consisting of a water condenser, Dry Ice condenser and a condensed volatile take-off mechanism. Uncondensed volatiles were scrubbed with water. The condenser was arranged such that no condensate could be returned to the column.

Attached to the bottom of the column was a reboiler fitted with a thermowell, a heater well, and a sink-trap shaped glass tube outlet terminated with a stopcock. The reboiler was heated with an internal cylindrical heating element connected to a variac® which was controlled by a thermoregulator. The reboiler contents were magnetically stirred. A constant level of liquid was maintained in the reboiler throughout the experiment.

The reboiler was charged with 211 g of 3-methacryloxypropyltrimethoxysilane (B) containing 150 ppm of phenothiazine and heated to approximately 116 degrees Celsius. Methanol (MeOH) was delivered at 0.83 ml/min to the top of the premixer (a 10 turn spiral condenser) where it mixed at ambient temperature with (A) which was being delivered at a rate of 4.76 ml/min. The MeOH/(A) mix entered the top of the column at 3 inches above the top bubble cap tray. Methanol was also delivered to the vaporizer at 2.06 ml/min. The methanol vapor then entered the column below the bottom bubble cap tray but above the reboiler. The reboiler temperature was maintained at 109 to 116 degrees Celsius. The temperature of the bottom 9 bubble caps varied from 70° to 76° C. The temperature at 12 inches above the MeOH/(A) feed point but below the condenser varied from 16° to 23° C. during the run.

In a period of 114.5 hours, a total of 39816 g (152.26 moles) of (A) and 15588 g (487.12 moles) of methanol were reacted resulting in 36928.8 grams of product. The product was analyzed by GLC to contain 93.5% 3-methacryloxypropyltrimethoxysilane and 4.69 percent methanol. The column and reboiler remained free of any gels during the entire operation.

EXAMPLE 2

This example is provided to show how higher reboiler temperatures can result in gellation.

Distilled 3-methacryloxypropyltrichloroilane (A) containing 0.015 wt. % phenothiazine was prepared according to U.S. Pat. No. 4,780,555 and was found to have a GLC purity of 98.2 percent monomer.

The apparatus used was a 40×1 inch column packed to a height of 35 inches with ⅛" glass helices supported by ceramic saddles. Directly over the column was a volatile condensation unit comprised of a water cooled overheads condenser and a Dry Ice condenser. The water condenser contained a magnetically controlled reflux mechanism. A reboiler containing a U-tube discharge, 40 Watt heater and magnetic stirrer were attached at the bottom of the column.

The reboiler was charged with 155.4 grams of 3-methacryloxypropyltrimethoxysilane (B) containing 1930 ppm of phenothiazine and heated to approximately 135° C. Methanol was vaporized and delivered to the center of the column, 16 inches below the liquid (A) feed point, at a liquid rate of 2.15 g/min. (A) was delivered 4 inches from the top of the column at a rate of 5.69 g/min. The reboiler temperature was maintained at 125° C. to 126° C. The temperature of the column at the point of the 3-methacryloxy- propyltrichlorosilane feed was 41° to 50° C. A reflux ratio of 16/4 was maintained during the operation.

After a period of 14 hours gels were visible in the column in and below the ceramic saddles. At 24 hours the column plugged and operation was discontinued.

EXAMPLE 3

For this example a 20 bubble cap tray column equipped with a condenser and reboiler as in example 1 was used.

A mixture of hexenyldimethylmethoxysilane and hexenyldimethylchlorosilane was placed in the reboiler and heated to approximately 130° C. Methanol was vaporized and fed to the column at a rate of approximately 2.0 g/min above the reboiler but below the bottom tray. Liquid hexenylmethyldichlorosilane (C) was fed to the top of the column at approximately 6 03 g/min. The reboiler was maintained at a temperature of 120° to 130° C. No reflux was observed in the head of the column.

The column was operated for 8 hours. Gas Chromotography (GC) of the resulting material showed 97 area % hexenylmethyldimethoxysilane (D). There was no evidence by GC of addition of HCl across the double bond or C=C isomerization.

EXAMPLE 4

The same apparatus used in example 1 was used in this example. The reboiler was charged with 219.6 g of methyl-3-methyldimethoxysilyl-2-methylpropionate (E) and heated to 130° C. Methanol was vaporized and fed to the column at a rate of 1.61 g/min. below the bottom tray and above the reboiler. Liquid methanol at a rate of 0.51 g/min was mixed with the chlorosilane being fed to the top of the column. Methyl-3-methyldichlorosilyl-2-methylpropionate (F) was fed to the column at a rate of approximately 7.25 g/min. The reboiler temperature was maintained at 125° to 131° C. which allowed the temperature in the lower ⅓ of the column to be maintained at 70° to 76° C. Temperatures at the head of the column varied from 20° to 33° C. No reflux was observed in the head of the column.

The column was operated until a total of 4422 8 of (E) and 1295.4 g of methanol were fed. A product of 90 area % purity (GC) was obtained. No residues were observed in the system.

EXAMPLE 5

A ⅞ inch by 43 inch column having a volume of 415 ml. was charged with 253.9 g of Amberlyst A-21 resin purchased from Rohm and Haas Corporation containing 55 percent water. The water was displaced by down flowing methanol through the bed. The methanol was then displaced with nitrogen. 3-Methacryloxypropyltrimethoxysilane produced in example 1 having an acid number of approximately 1.2 mg KOH/g was then pumped at a rate of 6.25 to 6.9 ml/min. to the top of the bed. Acid was observed at the bottom of the column after 10 to 15 hours of operation, at which time the bed was replaced. The resulting acid content of the 3-methacryloxypropyl- trimethoxysilane was 0.042 mg KOH/g.

What is claimed is:

1. A process for making organoalkoxysilanes using fractionation means consisting essentially of (i) a column comprised of contacting devices (ii) means for providing heat to and partially containing the contents at a sump portion and (iii) means for providing cooling to the contents at a head of the column; wherein the process comprises (A) feeding simultaneously into the column a) an organochlorosilane, (b) liquid alcohol and (c) vaporized alcohol, such that the alcohol contacts the organochlorosilane;

(B) maintaining a temperature within said column such that at least the lower ⅓ of the column is above the boiling point of the alcohol and no reflux of alcohol is present in the head of the column;

(B) recovering any organoalkoxysilane formed from the sump portion of the column; and (C) recovering HCl at the head of the column.

2. A Process as claimed in claim 1 wherein the alcohol is methanol.

3. A process as claimed in claim 1 wherein the alcohol is ethanol.

4. A process as claimed in claim 1 wherein the organochchlorosilane is 3-methacryloxypropyltrichlorosilane.

5. A process as claimed in claim 4 wherein a reboiler is used as the means to provide heat and the temperature of the reboiler contents is maintained between 70 to 115 degrees Celsius while operating under atmospheric pressure.

6. A process as claimed in claim 4 where the 3-methacryloxypropyltrichlorosilane additionally contains a compound which inhibits polymerization of the acryloxy group.

7. A process as claimed in claim 6 wherein the compound is phenothiazine.

8. A process as claimed in claim 7 wherein the phenolhiazine is present at levels equal to 50 to 500 parts per million parts organochlorosilane.

9. A process as claimed in claim 1 where the organochlorosilane is distilled prior to its introduction into the column.

10. A process as claimed in claim 1 wherein the contacting device comprises trays.

11. A process as claimed in claim 10 wherein the trays are bubble caps.

12. A process as claimed in claim 1 wherein the contacting device comprises packing.

13. A process as claimed in claim 1 wherein the contacting device comprises both packing and trays.

14. A process as claimed in claim 1 wherein the liquid alcohol comprises up to 40 percent of the total alcohol feed with the remainder of the alcohol being vaporized.

15. A process as claimed in claim 1 wherein the vaporized alcohol is fed into the sump portion of the column above said means for providing heat.

16. A process as claimed in claim 1 wherein the liquid alcohol is fed into the head of the column below said means for providing cooling.

17. A process as claimed in claim 16 wherein the liquid alcohol is combined with the organochlorosilane before being fed into the column.

18. A process as claimed in claim 1 wherein an excess of alcohol is continuously supplied.

19. A process as claimed in claim 18 wherein the alcohol is in an excess equal to 101 to 115 percent by weight of the theoretical amount of alcohol necessary for completion of the reaction.

20. A process as claimed in claim 1 wherein the organochlorosilane is hexenylmethyldichlorosilane.

21. A process as claimed in claim 1 wherein the organochlorosilane is methyl-3-methyldichlorosilyl-2-methylpropionate.

22. A method a claimed in claim 1 wherein additionally the organoalkoxysilanes prepared are contacted with an ion exchange resin that is free of hydroxylic materials, to remove any acid.

23. A method as claimed in claim 22 wherein the ion exchange resin is of the anionic type.

24. A method as claimed in claim 22 wherein the ion exchange resin contains reactive tertiary amine groups.

* * * * *